United States Patent
Morrison

(10) Patent No.: US 7,484,678 B2
(45) Date of Patent: Feb. 3, 2009

(54) NOZZLE FOR A NASAL INHALER

(75) Inventor: Robin Law Morrison, Barnard Castle (GB)

(73) Assignee: Glaxo Group Limited, Greenford, Middlesex (GB)

(*) Notice: Subject to any disclaimer, the term of this patent is extended or adjusted under 35 U.S.C. 154(b) by 193 days.

(21) Appl. No.: 10/553,688

(22) PCT Filed: Apr. 21, 2004

(86) PCT No.: PCT/EP2004/004243

§ 371 (c)(1), (2), (4) Date: Oct. 18, 2005

(87) PCT Pub. No.: WO2004/094068

PCT Pub. Date: Nov. 4, 2004

(65) Prior Publication Data
US 2006/0219813 A1    Oct. 5, 2006

(30) Foreign Application Priority Data
Apr. 24, 2003  (GB) ................... 0309354.9

(51) Int. Cl.
A62C 13/62 (2006.01)
B05B 7/32 (2006.01)

(52) U.S. Cl. .................... 239/302; 239/337
(58) Field of Classification Search ........... 239/302, 239/333, 337, 487, 489, 490, 482, 483, 488; 128/200.23, 200.14, 203.5, 203.21; 222/402.1
See application file for complete search history.

(56) References Cited
U.S. PATENT DOCUMENTS

| | | |
|---|---|---|
| 1,506,722 A | 6/1924 | Yunker |
| 2,435,605 A | 2/1948 | Rowell |
| 3,692,243 A * | 9/1972 | Breunsbach ............ 239/401 |
| 3,820,698 A | 6/1974 | Franz |
| 3,949,939 A | 4/1976 | Brown |
| 4,513,891 A | 4/1985 | Hain et al. |
| 4,515,315 A | 5/1985 | Corsette |
| 4,706,888 A | 11/1987 | Dobbs et al. |
| 4,801,093 A | 1/1989 | Brunet et al. |
| 4,946,069 A | 8/1990 | Fuchs |
| 4,961,727 A * | 10/1990 | Beard ..................... 604/75 |

(Continued)

FOREIGN PATENT DOCUMENTS

CA    2101049    5/1993

(Continued)

*Primary Examiner*—Davis D Hwu
(74) *Attorney, Agent, or Firm*—James P Riek

(57) ABSTRACT

There is provided a nasal dispensing nozzle for use with a fluid medicament discharge pump device having a discharge outlet for discharge of pumped fluid medicament. The nasal dispensing nozzle includes a body defining a fluid flow channel; an inlet port defining an inlet to the channel, the inlet port shaped for receipt of the discharge outlet to enable delivery of the pumped fluid medicament to the channel; and an outlet port defining an outlet from the channel, the outlet port shaped for insertion into the nasal cavity of a user to enable delivery of the pumped fluid medicament thereto. A screw thread path is provided to the channel between the inlet and the outlet to impart angular momentum to the pumped fluid medicament.

20 Claims, 7 Drawing Sheets

U.S. PATENT DOCUMENTS

| | | |
|---|---|---|
| 5,284,132 A | 2/1994 | Geier et al. |
| 5,497,946 A | 3/1996 | Laidler |
| 6,059,150 A | 5/2000 | Fuchs et al. |
| 6,234,365 B1 | 5/2001 | Bougamont et al. |
| 6,245,278 B1 | 6/2001 | Lausenhammer et al. |
| 6,585,172 B2 | 7/2003 | Arghyris |
| 7,080,759 B2 | 7/2006 | Petit |
| 2005/0072861 A1 | 4/2005 | Petit |

FOREIGN PATENT DOCUMENTS

| | | |
|---|---|---|
| DE | 960 777 C | 3/1957 |
| DE | 3712894 | 11/1988 |
| DE | 3731464 | 4/1989 |
| EP | 0 412 524 | 2/1991 |
| EP | 412524 | 2/1991 |
| EP | 0845299 | 5/2003 |
| EP | 1331036 | 7/2003 |
| EP | 1092447 | 1/2004 |
| FR | 1 340 235 A | 10/1963 |
| GB | 1318462 | 5/1973 |
| GB | 2372782 | 9/2002 |
| WO | 0178818 | 10/2001 |
| WO | 0276624 | 10/2002 |
| WO | 02096490 | 12/2002 |
| WO | 03045573 | 6/2003 |
| WO | 03078073 | 9/2003 |

\* cited by examiner

NOZZLE FOR A NASAL INHALER

This application is filed pursuant to 35 U.S.C. § 371 as a United States National Phase Application of International patent application Ser. No. PCT/EP2004/004243 filed Apr. 21, 2004, which claims priority from Great Britain application Ser. No. 0309354.9 filed in the United Kingdom on Apr. 24, 2003.

The present invention relates to a nozzle for use with a fluid dispensing device for nasal administration of medicament.

It is well known to provide a medicament dispenser device in which a fluid medicament formulation is dispensed as a spray via a nozzle to the nasal cavity of a user. In general, the fluid is delivered to the nozzle upon the application of user force to a fluid pumping mechanism. Such nasal dispensers may be arranged to dispense a single dose or may alternatively be arranged with a fluid reservoir from which individual metered doses may be pumped. A general example of such a pump action nasal inhaler device is shown and described in U.S. Pat. No. 4,946,069.

It is a problem with such pump action nasal spray devices that the characteristics of the spray are to an extent dependent upon the manner of actuation by the user. If the user actuates the device in a slow or lethargic manner then the dispensing of the fluid may be less spray-like than required for effective delivery to the nasal cavity. If the rate of discharge is too low full atomisation may not occur and the spray undesirably comprises of relatively large droplets of fluid. In extreme cases, no spray is produced and the fluid simply dribbles out from the tip of the nozzle.

To improve spray characteristics, it is known to be advantageous to provide a feature to the nozzle which causes acceleration of the fluid prior to its dispensing from the nozzle as a spray. Generally, an acceleration chamber is provided to the inner part of the nozzle. Additionally, shaped features and or inserts may be provided to the chamber (e.g. as part of or within the acceleration chamber) to cause the fluid to spin or swirl prior to its dispensing from the tip. In particular, the acceleration chamber may be arranged as a swirl chamber including a feature that acts on the fluid to cause swirling thereof. Such a feature may for example, take the form of a fixed multi-bladed propeller-shaped swirl insert.

The Applicant has now found an alternative method of creating swirl of the fluid prior to its dispensing. This method relies on the use of a defined screw thread feature within the inner part of the nozzle, which acts to define a screw-thread (i.e. helical) path through which fluid is pumped within the nozzle. The screw-thread channel acts such as to import angular momentum (i.e. swirl) to the liquid, which then emerges in swirling fashion. In developments of the method, the screw-thread channel may also be tapered or otherwise shaped such as to import acceleration to the pumped fluid. This method can be used as an alternative to the known use of a swirl chamber with swirl insert and can therefore result in simplified nozzle designs.

The Applicant has also observed that the screw thread channel feature of the nozzle of the present invention may also be employed to a meliorate the problem of fluid drain back within the nozzle. In more detail, it is known that that fluid pumped to the nozzle but not dispensed there from may under normal atmospheric pressure drain back down the interior of the nozzle and potentially into the fluid reservoir. This can lead to medicament precipitating out onto the sides of the nozzle interior and pump and also potentially to contamination of the contents of the reservoir by drained-back fluid material.

The Applicants have now found that the screw thread channel can act on the fluid to prevent its drain back within the nozzle. It is believed that the screw thread acts in threaded capillary fashion (i.e. it acts as an 'Archimdean screw') to lift up the fluid and thereby prevent the normal (but potentially problematic) draining back action.

It is an object of this invention to provide a nozzle for use in a fluid dispensing device that provides effective spraying from the nozzle.

It is a further object of this invention to provide a nozzle for use in a fluid dispensing device that provides reduced drain back of fluid from the nozzle.

European patent application no. EP-A-0 412 524 A1 describes a nozzle for a spray container comprising a swirl chamber comprising adjacent to the nozzle tip a tapered recess with swirl grooves extending outwardly therefrom.

According to a first aspect of the invention there is provided a nasal dispensing nozzle for use with a fluid medicament discharge pump device having a discharge outlet for discharge of pumped fluid medicament, the nasal dispensing nozzle comprising a body defining a fluid flow channel;

an inlet port defining an inlet to said channel, said inlet port shaped for receipt of said discharge outlet to enable delivery of said pumped fluid medicament to the channel; and an outlet port defining an outlet from said channel, said outlet port shaped for insertion into the nasal cavity of a user to enable delivery of the pumped fluid medicament thereto, wherein a screw thread path is provided to the channel between the inlet and said outlet to impart angular momentum to the pumped fluid medicament.

The term angular momentum is meant to encompass the terms spin and/or swirl and may occur in either a clockwise or anti-clockwise sense. Thus, the pumped fluid is spun and/or swirled as a result of its experience of being pumped through the screw thread path.

Suitably, the body also defines a hollow chamber locating between the screw thread path and the outlet. Thus, the spinning and/or swirling fluid is delivered to the chamber prior to its delivery from the outlet, and thence in use, to the nasal cavity of the user.

The present invention provides a nozzle for use with a nasal dispensing device for use in dispensing fluid form medicament to the nasal cavity of a user. The nozzle generally forms a component (either separable or integral) of a fluid medicament dispensing device, and the present invention therefore also provides a fluid medicament dispensing device incorporating the nozzle herein.

The nozzle is suitable for use with a fluid medicament discharge pump device having a discharge outlet for discharge of pumped fluid medicament. The fluid medicament discharge pump is generally comprised within a fluid medicament dispensing device as an integral or separable part thereof.

The nasal dispensing nozzle comprises a body defining a fluid flow channel. The channel acts to guide the flow of fluid form medicament through the nozzle for dispensing therefrom.

The exterior of the body is generally shaped both for engagement with a suitable fluid medicament discharge pump device (e.g. incorporated within a fluid medicament dispensing device) and for insertion into the nasal cavity of a user for delivery of fluid thereto.

The body is provided with an inlet port defining an inlet to the fluid flow channel. The inlet port shaped for receipt of the discharge outlet of a fluid discharge pump device to enable delivery of pumped fluid medicament to the channel.

The body is also provided with an outlet port defining an outlet from the fluid flow channel for dispensing therefrom. The outlet port, which generally takes the form of a tip to the nozzle, is shaped for insertion into the nasal cavity of a user to enable delivery of the pumped fluid medicament thereto.

In accord with the present invention a screw thread path is provided to the channel. The screw thread path locates between the inlet and the outlet and acts functionally to impart angular momentum to fluid medicament, as is pumped therethrough.

The screw thread path may be defined in a number of ways, as described hereinafter. The path is screw threaded. That is to say, it has the general (i.e. helical) form of a screw thread, which may follow either a clockwise or anti-clockwise screw path direction. The path generally comprises at least three, preferably at least five complete (i.e. 360°) screw turns, which a fluid will experience as it travels from the inlet to the outlet.

The screw thread path generally extends in symmetric fashion about a defined screw thread axis. Suitably, the screw thread axis corresponds to the pumping axis defined by the pump of the fluid discharge device. Suitably, fluid flow channel defined by the body of the nozzle is also symmetric about the screw thread axis. Suitably, the body of the nozzle further has an overall form that is symmetric about the screw thread axis.

The screw thread path may comprise a single screw threaded pathway. In other aspects however, the screw thread path comprises multiple screw threaded pathways, wherein generally each is arranged about a single (i.e. common) screw thread axis and in complementary fashion to the other. For example, a multiple-thread screw form path may be employed. Typically, from two to eight, particularly from three to six screw threaded pathways comprise the overall screw thread path.

The screw thread path is typically defined as an enclosed volume (i.e. space) of screw thread form. The enclosed volume is typically defined by the body of the nozzle and one or more inserts provided thereto. The inserts may in aspects, be reversibly removable from the body of the nozzle.

In a first aspect, the body defines a generally cylindrical channel having smooth walls and a cylindrical insert having a screw thread surface is snugly received thereby. The screw thread path is therefore defined in combination by the smooth walls of the body and the screw thread surface of the insert.

In a second aspect, the body defines a generally cylindrical channel having a screw thread surface defined therein and a cylindrical insert having smooth walls is snugly received thereby. In this aspect, the screw thread path is therefore defined in combination by the smooth walls of the insert and the screw thread surface of the body.

In a third aspect, the body defines a generally cylindrical channel having a screw thread surface and a cylindrical insert having an (imperfectly) mating screw thread surface is snugly received thereby. In general, the pitch of the screw thread surfaces of the body and insert are equivalent, but the depth (i.e. tread) of one surface is less than that of the other. When in mating contact, a screw thread path is therefore defined inbetween the relevant screw thread surfaces of the body and insert.

Preferably, the screw thread path is arranged decrease in cross-sectional area from the entrance thereto (i.e. at the inlet) to the exit thereto (i.e. at the outlet). The volume available to the fluid pumped therethrough progressively decreases and acceleration of the flow of the fluid therefore results. The decrease in cross-sectional area from entrance to exit may be achieved by progressively reducing the depth (i.e. tread) of the screw thread or by progressively reducing the width of the screw thread or by progressively reducing the pitch of the screw thread or by a combination of these reductions.

In one aspect, the decrease in cross-sectional area is achieved by tapering the screw thread path. Thus, in variations of each of the three aspects above, the screw thread path is suitably tapered by reducing the depth (i.e. tread) or width or both of the relevant screw thread surface. In the case of the first aspect the relevant screw thread surface is on the insert. In the case of the second aspect the relevant screw thread surface is on the body and in the case of the third aspect the relevant screw thread surface is on either or both of the body and insert.

In one particular aspect, the screw thread path is suitably tapered by keeping the screw thread surface (of as appropriate, either the body or the insert or both) constant but allowing that screw thread surface to progressively cut into the smooth walls (of as appropriate, either the body or the insert).

In one aspect, the outlet of the dispensing nozzle is provided with a reversible stopper. The stopper acts such as to prevent drain back of delivered fluid from the dispensing nozzle (in particular, from the area at the tip of the nozzle and generally adjacent to the dispensing outlet) and may therefore in this respect, complement the threaded capillary action of the screw thread path. The stopper is reversibly mountable to the nozzle (e.g. at the tip) and may have any suitable shape including disc shaped, wherein the disc may be flat, or in aspects have a convex or concave form.

It will be appreciated that the stopper is generally shaped for effective sealing engagement with the tip of the dispensing nozzle (i.e. that area proximal to the dispensing orifice) and therefore that the shaping of the stopper may be arranged to inversely mirror that of the nozzle tip.

The stopper may be formed from any suitable material including those with plastic properties, particularly those with resilient properties. Stoppers made from synthetic and naturally occurring polymers including rubber are herein envisaged.

According to another aspect of the present invention there is provided a housing assembly for reversible receipt of a fluid medicament discharge device for spraying a fluid medicament into a nasal cavity, the housing assembly comprising a body defining a cavity; and engageable with said body, a dispensing nozzle as described herein.

In use, a fluid discharge device typically houses in the cavity, and in combination the housing assembly and fluid discharge device comprise a fluid dispensing device. Alternative embodiments are envisaged in which the fluid discharge device is either integral with or reversibly removable from the housing assembly of the fluid dispensing device.

The fluid discharge device typically has a hollow casing defining a reservoir for containing a volume of fluid and a pump having a suction inlet extending within the hollow casing, the pump having a discharge outlet extending from a first end of the hollow casing for co-operation with the dispensing nozzle to enable pumped delivery of fluid from the reservoir to the dispensing nozzle.

It will be appreciated that in general operation of the fluid dispensing device relative movement between the hollow casing and the pump acts such as to pump fluid from the fluid reservoir into the dispensing nozzle for dispensing therefrom. The fluid reservoir typically contains several doses of fluid form medicament.

In aspects, the pumping is metered. For example, each pumping action results in delivery of a single dose of fluid from the reservoir to the nozzle.

Suitably for metered delivery, the pump includes a plunger, which is slideable in a metering chamber located within the hollow casing, the metering chamber being sized to accommodate a single dose of fluid.

Suitably, the pump comprises a pre-compression pump, such as a VP3, VP7 or modifications, model manufactured by Valois S A. Typically, such pre-compression pumps are used with a bottle (glass or plastic) capable of holding 8-50 ml of a formulation. Each spray will typically deliver 50-100 µl of such a formulation and the device is therefore capable of providing at least 100 metered doses.

The device may further comprise a protective end cap having an inner surface for engagement with the body. The end cap is moveable from a first position in which it covers the nozzle to a second position in which the nozzle is uncovered.

In one aspect, a stopper locates on the end cap such that when the end cap is in the first (i.e. protective) position the stopper engages the nozzle to seal the nozzle orifice and thereby prevent drain back. In the second (i.e. in-use position) the stopper is disengaged from the nozzle such that the nozzle orifice is no longer sealed.

The stopper may form an integral part of the end cap or alternatively, the stopper may mount to the end cap. Any suitable method of mounting is envisaged including adhesive, snap-fit and weld mounting.

In general, the stopper locates in the inner part of the end cap. In one aspect, the inner part of the end cap is provided with annular walls defining a cavity for receipt of the stopper as an insert thereto. The stopper insert may be simply be mechanically inserted or it may be adhesively or otherwise fixed.

Suitable stopper insert forms may be formed in a variety of ways. In one aspect, a rubber disc-shaped stopper is stamped from a sheet of rubber. In another aspect, a disc-shaped stopper is moulded (e.g. by an injection moulding process). In a further aspect, the protective end cap is moulded and the stopper is then moulded within the formed end cap (i.e. a 'two shot' moulding process).

The hollow casing of the fluid dispensing device may take any suitable form. Suitably, several lugs are formed on the hollow casing for engagement with complementary projections formed on the inner surface of the end cap, each of the lugs being arranged to extend through a longitudinally extending slot formed in the side wall of the body.

In one aspect, the hollow casing may have at least one outwardly extending detent for engagement with a complementary recess formed in the inner surface of the end cap so as to releasable hold the end cap in position on the body. Each detent may extend through a respective longitudinally extending slot in the body for engagement with the respective recess formed in the end cap.

According to a still further aspect of the present invention there is provided a kit of parts comprising a housing assembly as described above and a fluid discharge device receivable thereby.

It is also envisaged that the housing assembly could be supplied as a separate item, into which a user or pharmacist later fits a suitable fluid discharge device.

It will be appreciated that whilst the present invention has been particularly described in terms of a nozzle suitable for delivery of fluid medicament to a nasal cavity, that variations of the invention are possible to enable delivery into other body cavities (e.g. the ear or eye).

The invention will now be described further with reference to the accompanying drawing in which.

Figure 1:
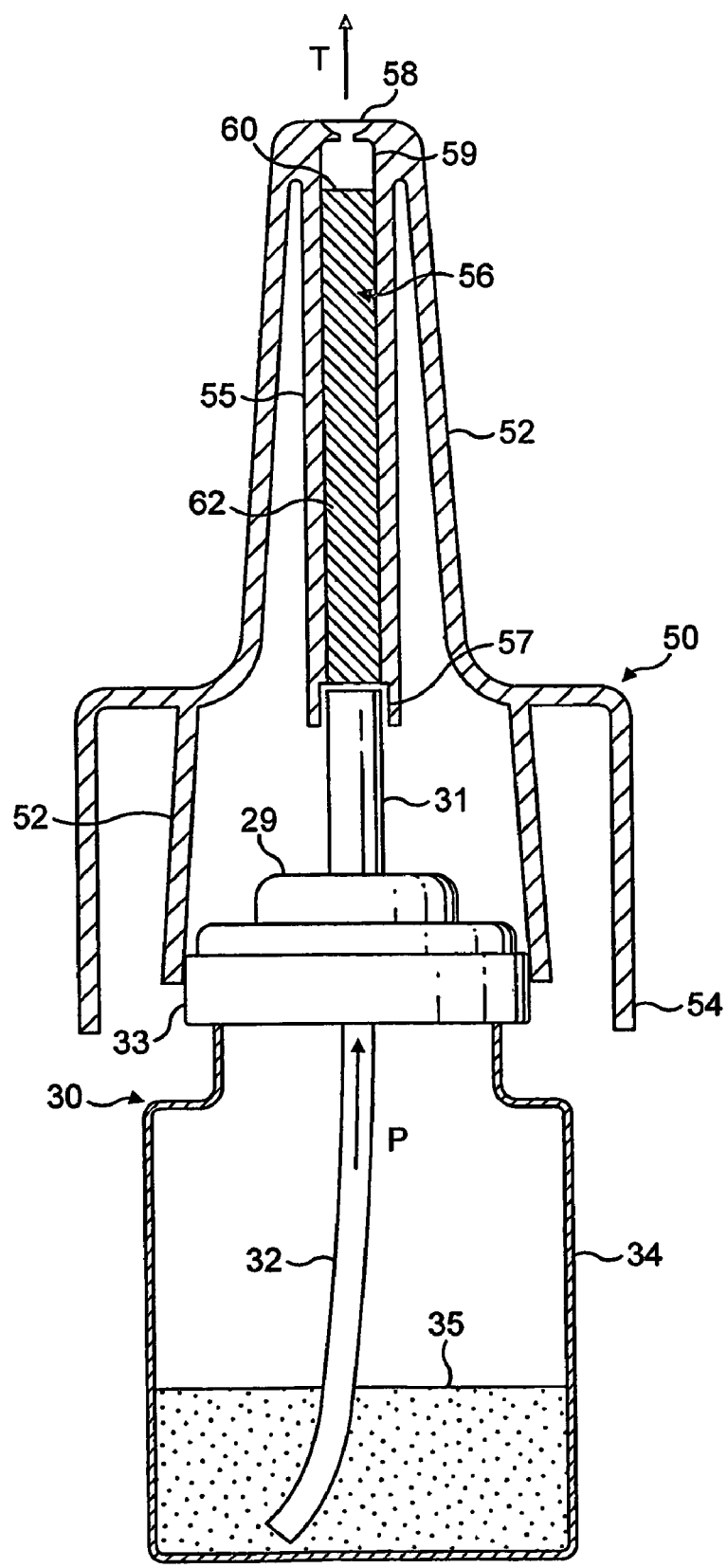
FIG. 1 is a cross-sectional view of a dispensing nozzle herein in engaging contact with a fluid medicament discharge pump device.

With reference to FIG. 1 there is shown a dispensing nozzle 50 in engaging contact with a fluid medicament discharge pump device 30.

The fluid medicament discharge device 30 is of standard form and comprises a container 34 for storing the fluid form medicament 35 to be dispensed and a compression pump 29 having a suction inlet 32 located within the container 30 and a discharge outlet 31 for transferring fluid from the pump 29 to the nozzle 50. The compression pump 29 is actuable along a pumping axis designated 'P' in response to force applied to the container 34 to move it towards the nozzle 50 so as to compress the pump 29.

The body 52 of the nozzle 50 is provided with first cylindrical sleeve 52 for receiving collar 33 provided to the neck of the container 30. The body 52 of the nozzle 50 is also provided with a second cylindrical sleeve 54 concentric with the first cylindrical sleeve 52 shaped for engagement with a housing (not shown) for housing the fluid medicament discharge device 30.

Smooth cylindrical inner wall 55 of the body 52 of the nozzle 50 further defines a cylindrical fluid flow channel 56 having an inlet 57 and dispensing outlet 58. It will be seen that the inlet 57 is shaped to snugly receive the discharge outlet 31 of the fluid discharge pump device 30, which is in abutting contact therewith. An insert 60 having plural screw threads 62 provided to the surface thereof is snugly received within the fluid flow channel 56. The insert occupies 60 the bulk of the channel 56, although a chamber 59 adjacent to the dispensing outlet 58 remains open (i.e. it comprises 'free space'). In combination, the smooth cylindrical wall 55 and the screw threaded surface 62 of the insert define a screw thread path such that in use, fluid medicament 35 pumped into the channel 55 at the inlet 57 initially experiences the screw thread path, which imparts angular momentum thereto before the fluid enters the chamber 59 and finally being dispensed from the dispensing outlet 58.

It will be seen that both the screw threaded surface 62 of the insert 60 and the cylindrical wall 55 of the body and hence, also the screw thread path are all symmetric about screw thread axis designated 'T'. The screw thread axis 'T' is also co-axial with pumping axis 'P'.

Figure 2A:
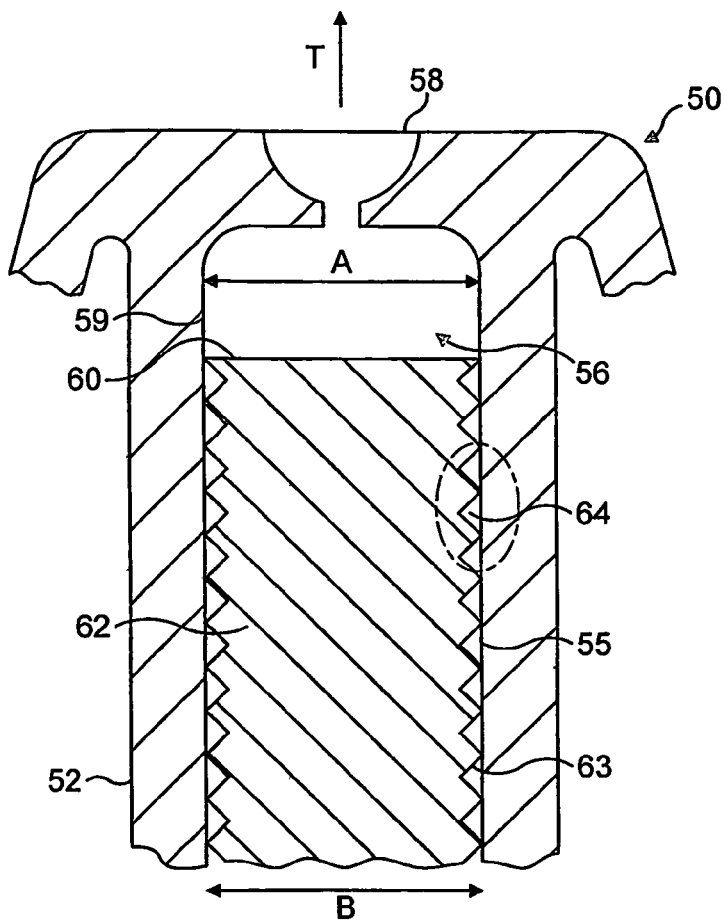
FIG. 2a is a cross-sectional view of a detail of the dispensing nozzle of FIG. 1.
Figure 2B:
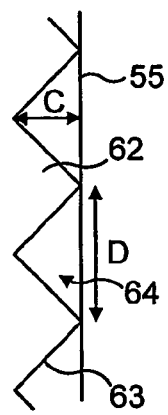
FIG. 2b is a cross-sectional view of an extreme detail of the dispensing nozzle of FIG. 1.

The characteristics of the screw thread path of the nozzle 50 of FIG. 1 may be better understood by reference to FIGS. 2a and 2b. FIG. 2a show an enlarged view of the dispensing tip part of the nozzle 50 of FIG. 1. FIG. 2b shows a further enlargement of part of FIG. 2a to show the engagement of a single tooth 63 of the screw thread 62 with the cylindrical wall 55 of the body 52 to define screw thread path 64.

With reference to FIG. 2a the diameter 'A' of the fluid flow channel 56 defined by the cylindrical smooth wall 55 of the body 52 may be seen to be constant throughout. The diameter 'B' of the insert 60 with screw thread surface 62 is also constant throughout and essentially equivalent to the diameter 'A' of the fluid flow channel.

With reference to FIG. 2b, the depth (or tread) 'C' and the width (or pitch) 'D' of the screw thread path 64 defined by tooth 63 of the screw thread surface 62 is also constant throughout.

In accord with the present invention any of the distances A, B, C or D may be varied to define a tapering screw thread path, which in use, acts on fluid pumping through the path to cause accelerated flow thereof.

Figure 3:
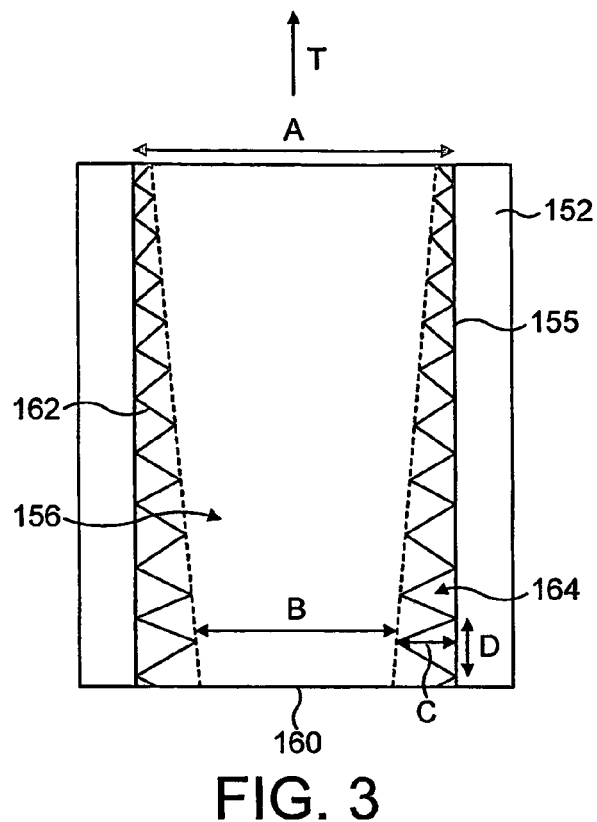
FIG. 3 is a cross-sectional view of the fluid flow channel of a second dispensing nozzle herein having a screw thread path of non-uniform cross-sectional area.

FIG. 3 shows a view of a detail of a second nozzle embodiment herein, in which the body 152 of the nozzle defines a smooth cylindrical wall 155 of uniform diameter 'A' throughout, thereby defining a fluid flow channel 156 also of uniform diameter 'A'. Within the channel 156 sits insert 160 having a screw threaded surface 162. The diameter 'B' of the insert progressively increases moving along screw thread axis 'T' such as to give the insert 160 an overall tapered form. As a result of the tapering, the tread 'C' of the screw thread path 164 decreases moving along the screw thread axis 'T', whereas the pitch 'D' remains constant. The overall effect is that the cross-sectional area of the screw thread path 164 progressively decreases moving along the screw thread axis 'T' such that fluid pumped therethrough will experience accelerated flow.

Figure 4:
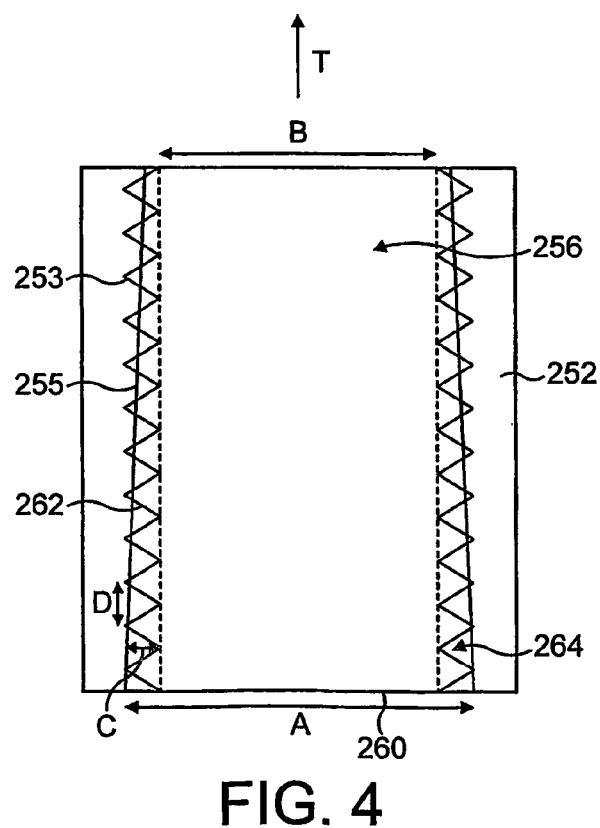
FIG. 4 is a cross-sectional view of the fluid flow channel of a third dispensing nozzle herein having a screw thread path of non-uniform cross-sectional area.

FIG. 4 shows a view of a detail of a third nozzle embodiment herein, in which the body 252 of the nozzle defines a cylindrical wall 255 of progressively decreasing diameter 'A' on moving along screw thread axis 'T'. The wall also has a screw thread surface 253 cut therein, wherein the tread of the screw thread surface progressively increases on moving along screw thread axis 'T'. Thus, overall the wall 252 and its screw thread surface 253 define an inwardly tapering fluid flow channel 256 with increasingly deep thread characteristics.

Within the channel 256 sits there is received insert 260 of constant diameter 'B'. The insert 260 also has a screw threaded surface 262 shaped for screw-in receipt by the screw thread surface 253 of the wall 255 of the body 252. A screw thread path 264 is defined by the mating screw thread surfaces 253, 262. As a result of the tapering of the wall 255 (and hence, the fluid flow channel 256 defined thereby), the tread 'C' of the screw thread path 264 decreases moving along the screw thread axis 'T', whereas its pitch 'D' remains constant. The overall effect is that the cross-sectional area of the screw thread path 264 progressively decreases moving along the screw thread axis 'T' such that fluid pumped therethrough experiences accelerated flow.

Figure 5:
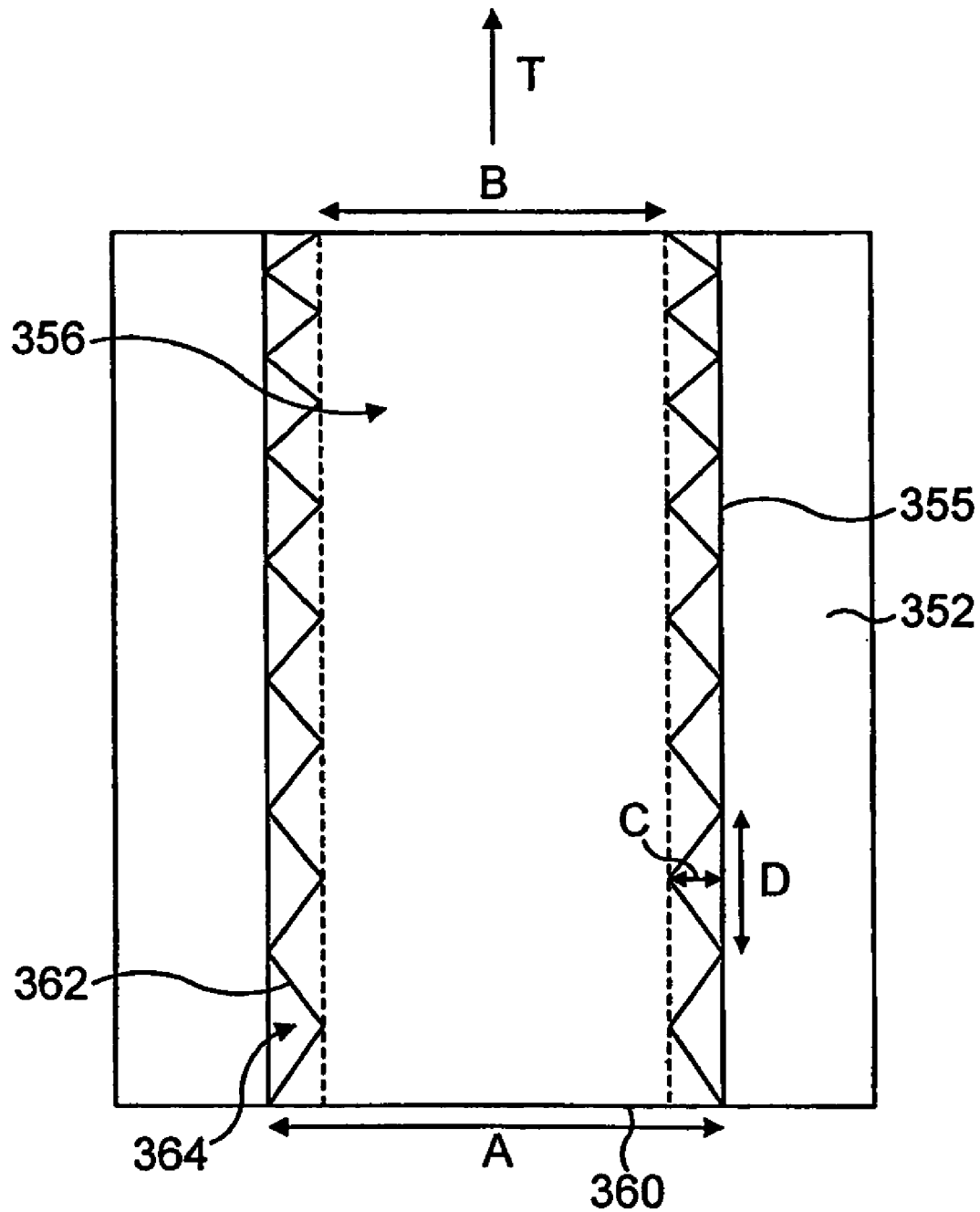
FIG. 5 is a cross-sectional view of the fluid flow channel of a fourth dispensing nozzle herein having a screw thread path of non-uniform cross-sectional area.

FIG. 5 shows a view of a detail of a fourth nozzle embodiment herein, in which the body 352 of the nozzle defines a smooth cylindrical wall 355 of uniform diameter 'A' throughout, thereby defining a fluid flow channel 356 also of uniform diameter 'A'. Within the channel 356 sits insert 360 having a screw threaded surface 362 of uniform diameter 'B'. A screw thread path 364 is defined by the wall 355 and the screw thread surface 362 of the insert 360. The pitch 'D' of the screw thread path 364 decreases moving along the screw thread axis 'T', whereas its tread 'C' remains constant. The overall effect is that the cross-sectional area of the screw thread path 364 progressively decreases moving along the screw thread axis 'T' such that fluid pumped therethrough will experience accelerated flow.

Figure 6:
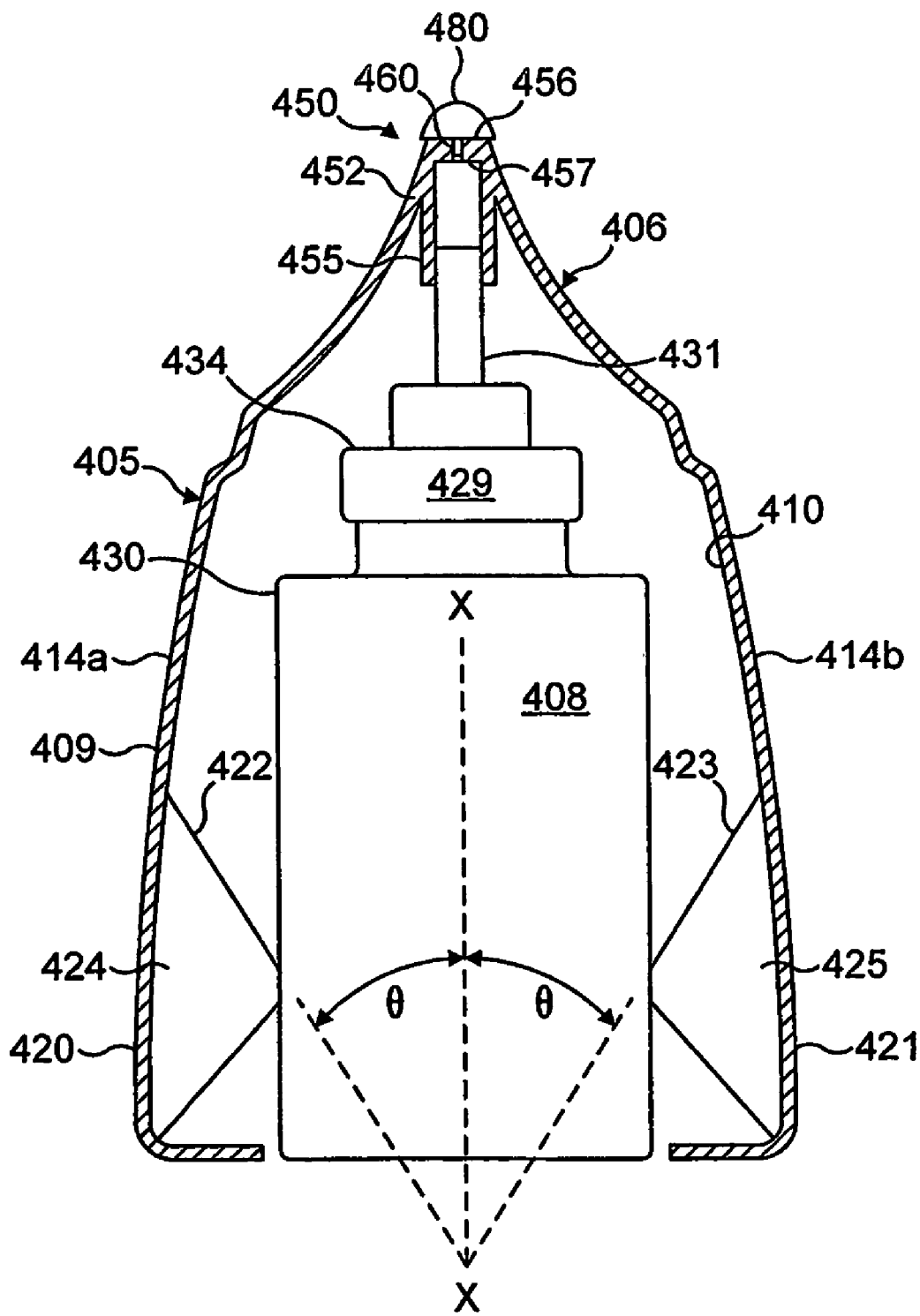
FIG. 6 is a cross-sectional view through a first embodiment of a fluid dispensing device according to the invention in a storage state.
Figure 7:
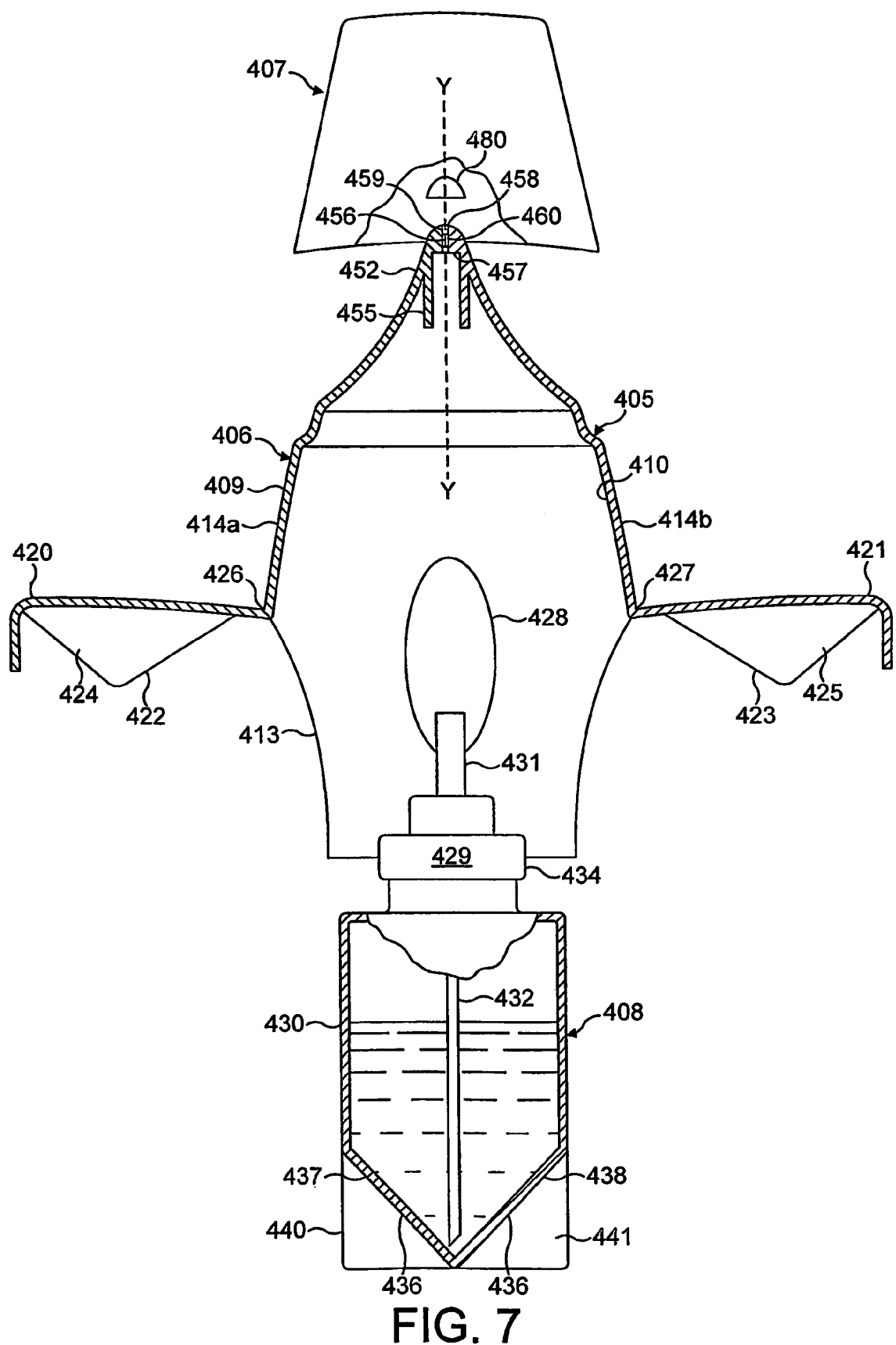
FIG. 7 is a cross-section similar to that shown in FIG. 7 but showing the insertion of a fluid discharge device according to a second aspect of the invention into a housing assembly according to a third aspect of the invention.
Figure 8:
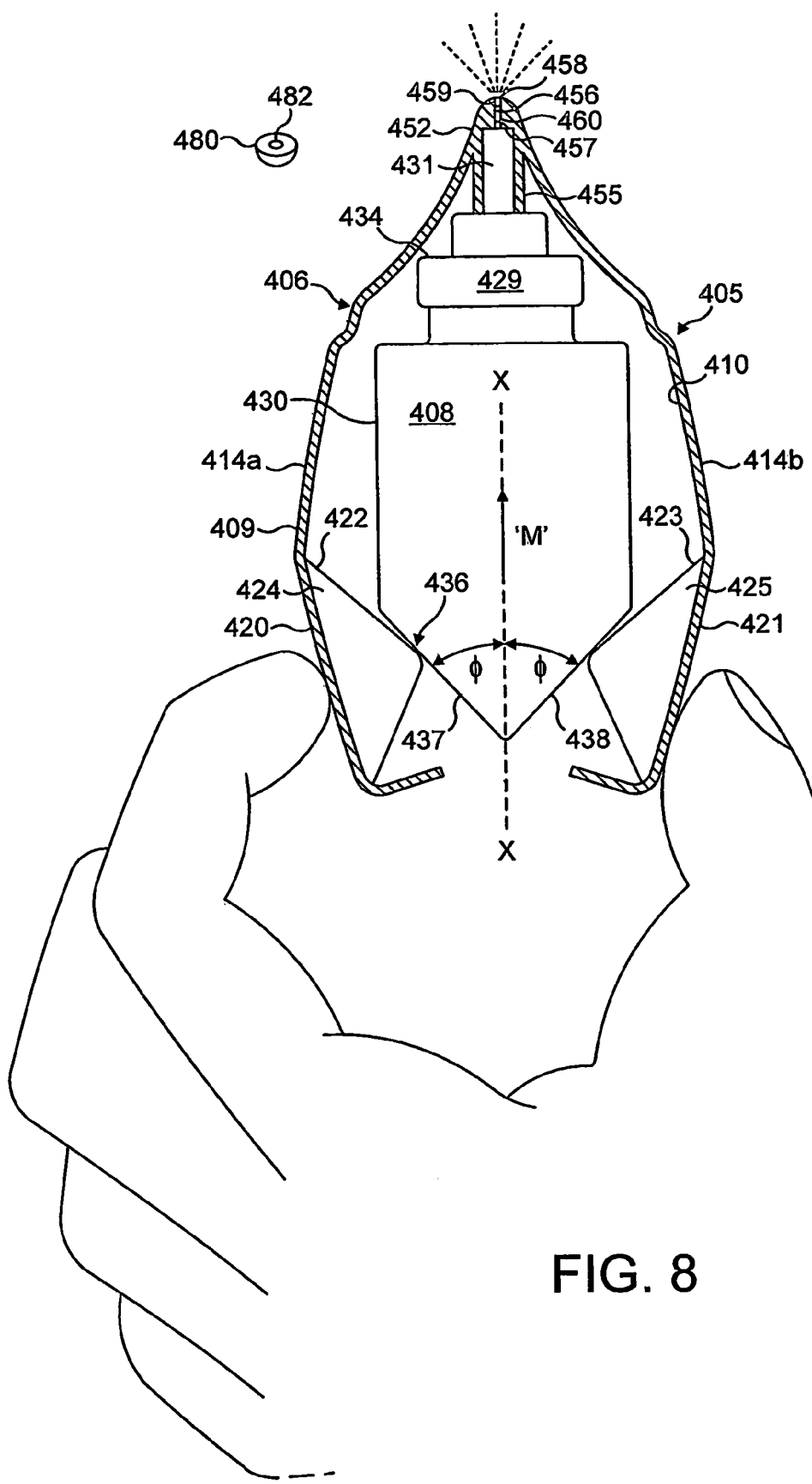
FIG. 8 is a cross-section similar to that of FIG. 6 but showing the fluid dispensing device in a use state.

With reference to FIGS. 6 to 8 there is shown a first embodiment of a fluid dispensing device 405 for spraying a fluid into a body cavity comprising a housing 409, a nozzle 450 for insertion into a body cavity, a fluid discharge device 408 moveably housed within the housing 409, the fluid discharge device 408 comprising a container 430 for storing the fluid to be dispensed and a compression pump 429 having a suction inlet 432 located within the container 430 and a discharge outlet 431 for transferring fluid from the pump 429 to the nozzle 450 and finger operable means 420, 421 to apply a force to the container 430 to move the container 430 towards the nozzle 450 so as to actuate the pump 429. The finger operable means being in the form of two opposing levers 420, 421 each of which is pivotally connected to part of the housing 409 and is arranged to act upon a base portion 436 of the container 430 so as to urge the container 430 towards the nozzle 450 when the two levers 420, 421 are squeezed together by a user.

In more detail the fluid dispensing device 405 comprises of a plastic moulded body 406 and the fluid discharge device 408 and further comprises of a protective end cap 407 having an inner surface for engagement with the body 406 to protect the dispensing nozzle 450.

The body 406 is made from a plastic material such as polypropylene and defines a housing 409 and dispensing nozzle 405 so that the housing 409 and body 452 of the nozzle 405 are made as a single plastic component. The housing 409 defines a cavity 410. The dispensing nozzle 450 is connected to one end of the housing 409, extends away from the housing 409 and has an external tapering form.

The discharge outlet from the pump 429 is in the form of a tubular delivery tube 431 and a tubular guide in the form of an outlet tube 455 is formed within the nozzle 450 to align and locate the delivery tube 431 correctly with respect to the nozzle 450.

An annular abutment 457 is formed at the end of the outlet tube 455. The annular abutment 457 defines the entry to a fluid flow chamber 456 through which fluid is be dispensed in use and is arranged for abutment with an end of the delivery tube 431.

A screw threaded insert 460 is snugly received within the fluid flow channel 456 of the nozzle 450. The insert occupies 460 the bulk of the channel 456, although a chamber 459 adjacent to the dispensing outlet 458 remains open (i.e. it comprises 'free space'). In combination, the outlet tube 455 and the screw threaded insert 460 define a screw thread path such that in use, fluid medicament 435 pumped into the channel 455 at the inlet 457 initially experiences the screw thread path, which imparts angular momentum thereto before the fluid enters the chamber 459 and finally being dispensed from the dispensing outlet 458. The general form of the fluid flow chamber 456 and insert 460 may be appreciated to be very similar to that shown in FIG. 1.

In the storage state of FIG. 6, rubber hemispherical nozzle stopper end 480 is reversibly mounted on annular abutment 417 to seal the nozzle outlet 458.

The fluid discharge device 408 has a longitudinal axis X-X and each of the levers 420, 421 has an abutment surface 422, 423 arranged at an angle θ to the longitudinal axis X-X of the fluid discharge device 408 for abutment against a base portion 436 of the container so as to convert a force applied to the levers 420, 421 substantially transversely to the longitudinal axis X-X of the fluid discharge device 408 into a force along the longitudinal axis X-X of the fluid discharge device 408. This arrangement allows a standard fluid discharge device to be used without modification.

The nozzle 450 has a longitudinal axis Y-Y and the longitudinal axis X-X of the fluid discharge device 408 is aligned with the longitudinal axis Y-Y of the nozzle 450. This has the advantage that when the pump 429 is actuated the force applied to the tubular delivery tube 431 is along the axis of the tubular delivery tube and no bending or deflection of the delivery tube 431 will occur due to the applied force.

At least part of the surface of the base portion 436 of the container 430 is inclined at an angle Φ with respect to the longitudinal axis X-X of the fluid discharge device 408 so as to form an inclined surface, the or each inclined surface being arranged to be acted upon by the levers 420, 421 so as to convert a force applied to the levers 420, 421 substantially transversely to the longitudinal axis X-X of the fluid discharge device 408 into a force along the longitudinal axis X-X of the fluid discharge device 408.

The base portion 436 of the container 430 has two inclined surfaces 437, 438 each arranged for co-operation with a respective one of the levers 420, 421. The inclined surface 437 is arranged to co-operate with the abutment surface 422 and the inclined surface 438 is arranged to co-operate with the abutment surface 423. The abutment surface 422 is formed by an edge of a web 424 formed as part of the lever 420 and the abutment surface 423 is formed by an edge of a web 425 formed as part of the lever 421.

Each of the levers 420, 421 is pivotally connected to part of the housing 409 by a respective living hinge. In the embodiment shown each of the levers 420, 421 is pivotally connected to a respective one of the two side walls 414*a*, 414*b* by a respective living hinge 426, 427.

The fluid discharge device 408 has a hollow container 430 defining a reservoir containing several doses of the fluid to be dispensed and a compression pump 429 attached to one end of the container 430. The container 430 as shown is made from a translucent or transparent plastics material however it will be appreciate that it could be made from other translucent or transparent materials such as glass.

The container 430 has two or more supports to allow the container to be stood up on the base portion 436 and as shown two supports 440, 441 are moulded as an integral part of the container 430. These supports are useful in that, because the base portion 436 is made up of two inclined surfaces 437, 438, it could not normally be stood up vertically.

The pump 429 includes a plunger (not shown) slidingly engaged within a pump casing 434 which defines a chamber (not shown) sized to accommodate a single dose of fluid. The plunger is attached to the tubular delivery tube 431 which is arranged to extend from one end of the pump 429 for co-operation with the outlet tube 456 of the dispensing nozzle 450. The plunger includes a piston (not shown) slidably supported in the chamber formed in the pump casing 434.

The fluid is discharged through a discharge channel defined by the tubular delivery tube 431 into the fluid flow channel 456 of the dispensing nozzle 450.

The size of chamber is such that it accommodates a single dose of fluid, the diameter of the chamber and piston combined with the stroke of the plunger being such that a full stroke of the plunger in the chamber will produce a change in volume equal to a single dose of fluid.

The pump casing 434 is connected to the container 430 such that when the piston is moved by a return spring (not shown) into a start position a new dose of fluid is drawn into the cylinder via the suction inlet in the form of a pick-up tube 432 from the container 430 ready for discharge.

The tapering form of the base portion 436 of the container 430 is advantageous in that it allows the pick up tube 432 to collect, without special orientation of the container, more fluid than if a flat bottomed container is used.

The end cap 407 is a tubular component, which is closed at one end and has a thin flexible side wall which defines a cavity into which the nozzle 450 is engaged to protect the nozzle 450 from damage.

FIG. 7 shows the fluid dispensing device 405 in a partly assembled state in which the two levers 420,421 have been moved into a loading position to allow the fluid discharge device 408 to be inserted into the cavity 410 in the housing 409. In the partly assembled state, the stopper end 480 has been removed from the annular abutment end 417 of the nozzle 450 to unseal the orifice 458.

From the position shown the fluid discharge device 408 is moved upwardly until the delivery tube 431 fully engages with the outlet tube 416. The two levers 420, 421 are then folded down into the position shown in FIG. 6 such that end portions of the abutment surfaces 422, 423 abut gently against the inclined surfaces 437, 438 of the container 430. The levers 420, 421 in this position are used to hold the fluid discharge device 408 within the housing 409.

As shown in FIG. 8, in use, the end stopper 480 is removed from the annular abutment end 417 of the nozzle 450 to unseal the orifice 458. The end stopper 480 is shown in up-ended view in which inner cavity 482 may be seen. It will be appreciated that the cavity 482 is sized and shaped for effective, snug receipt by the annular nozzle 450 end to ensure good sealing of the orifice 458.

To enable dispensing of fluid, a user first grasps the fluid dispensing device 405 by the two levers 420, 421. Provided that only a light pressure is applied to the levers 420, 421 no fluid will be discharged and the user is able to manoeuvre the dispensing nozzle 450 of the fluid dispensing device 405 into the body orifice into which fluid is required to be dispensed.

If the user then squeezes the two levers 420, 421 together with increasing force the interaction of the abutment surfaces 422, 423 with the inclined surfaces 437, 438 causes the container 430 to be moved towards the nozzle 450 as indicated by the arrow 'M' on FIG. 8.

However, the abutment between the end of the delivery tube 431 and the annular abutment 417 will prevent movement of the delivery tube 431 in the same direction. This effect of this is to cause the delivery tube 431 to push the plunger into the pump casing 434 thereby moving the piston of the pump in the cylinder. This movement causes fluid to be expelled from the cylinder into the delivery tube 431. The fluid forced into the delivery tube is then transferred into the fluid flow chamber 456 of the nozzle 450 from where it is expelled as a fine spray into the body orifice.

Upon releasing the pressure applied to the levers 420, 421 the delivery tube 431 is urged out of the pump casing by the internal return spring and causes fluid to be drawn up the pick-up tube 432 to re-fill the cylinder.

The actuating procedure can then be repeated until all of the fluid in the container has been used. However, only one or two doses of fluid are normally administered at a time.

After use, the end stopper 480 will be replaced on the annular end 417 of the nozzle 450 to seal the orifice 458 and, acting in tandem with the screw thread insert 460, prevent drain back of fluid to the delivery tube 431.

When the container 430 is empty a new fluid discharge device 408 is loaded into the housing 409 thereby restoring the fluid dispensing device 405 into a useable condition.

Administration of medicament may be indicated for the treatment of mild, moderate or severe acute or chronic symptoms or for prophylactic treatment. It will be appreciated that the precise dose administered will depend on the age and condition of the patient, the particular medicament used and the frequency of administration and will ultimately be at the discretion of the attendant physician. When combinations of medicaments are employed the dose of each component of the combination will in general be that employed for each component when used alone.

The fluid dispensing device herein is particularly suitable for dispensing a fluid medicament formulation. The container therefore contains a fluid medicament formulation e.g. formulated either as a solution formulation or as a suspension formulation comprising a suspension of active medicament particles in an inert suspending formulation.

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (eg as the sodium salt), ketotifen or nedocromil (eg as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone (eg as the furoate ester), ciclesonide, triamcinolone (eg as the acetonide), 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester or 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; PDE4 inhibitors eg cilomilast or roflumilast; leukotriene antagonists eg montelukast, pranlukast and zafirlukast; [adenosine 2a agonists, eg 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate)]*; [α4 integrin inhibitors eg (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino] propanoic acid (e.g as free acid or potassium salt)]*, diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagons. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the medicament is an anti-inflammatory compound for the treatment of inflammatory disorders or diseases such as asthma and rhinitis.

In one aspect, the medicament is a glucocorticoid compound, which has anti-inflammatory properties. One suitable glucocorticoid compound has the chemical name: 6α, 9α-Difluoro-17α-(1-oxopropoxy)-11β-hydroxy-16α-methyl-3-oxo-androsta-1,4-diene-17β-carbothioic acid S-fluoromethyl ester (fluticasone propionate). Another suitable glucocorticoid compound has the chemical name: 6α, 9α-difluoro-17α-[(2-furanylcarbonyl)oxy]-11β-hydroxy-16α-methyl-3-oxo-androsta-1,4-diene-17β-carbothioic acid S-fluoromethyl ester. A further suitable glucocorticoid compound has the chemical name: 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

Other suitable anti-inflammatory compounds include NSAIDs e.g. PDE4 inhibitors, leukotriene antagonists, iNOS inhibitors, tryptase and elastase inhibitors, beta-2 integrin antagonists and adenosine 2a agonists.

The medicament is suitably in particulate form. The particulate medicament suitably has a mass mean diameter (MMD) of less than 20 μm, preferably between 0.5-10 μm, especially between 1-5 μm. If particle size reduction is necessary, this may be achieved by techniques such as micronisation, wet bead milling and/or microfluidisation.

Suitable medicament particles may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

In one aspect, the fluid medicament formulation is formulated as a medicament suspension formulation comprising a suspension of active medicament particles in an inert suspending formulation, optionally containing other pharmaceutically acceptable additive components.

The inert suspending formulation is typically aqueous and comprises one or more excipients. By the term "excipient", herein, is meant substantially inert materials that are non-toxic and do not interact with other components of a composition in a deleterious manner including, but not limited to, pharmaceutical grades of carbohydrates, organic and inorganic salts, polymers, amino acids, phospholipids, wetting agents, emulsifiers, surfactants, poloxamers, pluronics, and ion exchange resins, thixotropic agents and combinations thereof.

Suitable carbohydrates include monosaccharides including fructose; disaccharides, such as, but not limited to lactose, and combinations and derivatives thereof; polysaccharides, such as, but not limited to, cellulose and combinations and derivatives thereof; oligosaccharides, such as, but not limited to, dextrins, and combinations and derivatives thereof; polyols, such as but not limited to sorbitol, and combinations and derivatives thereof.

Suitable organic and inorganic salts include sodium or calcium phosphates, magnesium stearate, and combinations and derivatives thereof.

Suitable polymers include natural biodegradable protein polymers, including, but not limited to, gelatin and combinations and derivatives thereof; natural biodegradable polysaccharide polymers, including, but not limited to, chitin and starch, crosslinked starch and combinations and derivatives thereof; semisynthetic biodegradable polymers, including, but not limited to, derivatives of chitosan; and synthetic biodegradable polymers, including, but not limited to, polyethylene glycols (PEG), polylactic acid (PLA), synthetic polymers including but not limited to polyvinyl alcohol and combinations and derivatives thereof;

Suitable amino acids include non-polar amino acids, such as leucine and combinations and derivatives thereof. Suitable phospholipids include lecithins and combinations and derivatives thereof.

Suitable wetting agents, surfactants and/or emulsifiers include gum acacia, cholesterol, fatty acids including combinations and derivatives thereof. Suitable poloxamers and/or Pluronics include poloxamer 188, Pluronic® F-108, and combinations and derivations thereof. Suitable ion exchange resins include amberlite IR120 and combinations and derivatives thereof;

Preferred suspension formulations herein comprise an aqueous suspension of particulate medicament and one or more additional components selected from the group consisting of suspending agents, preservatives, wetting agents, viscosity enhancing agents and isotonicity adjusting agents.

Suitable suspending agents include carboxymethylcellulose, veegum, tragacanth, bentonite, methylcellulose and polyethylene glycols.

Particular suspending agents are those sold under the trade name Miglyol by Condea Chemie GmbH wich comprise ester oils of saturated coconut and plam oil-derived caprylic and capric fatty acids and glycerin or propylene glycol. Particular examples include Miglyol 810, Miglyol 812 (caprylic/capric trigltceride); Miglyol 818 (caprylic/capric/linoleic triglyceride); Miglyol 829 (caprylic/capric/succinic triglyceride); and Miglyol 840 (propylene glycol dicaprylate/dicaprate).

Suitable preservatives include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts and polymyxin.

Suitable wetting agents function to wet the particles of medicament to facilitate dispersion thereof in the aqueous phase of the composition. Examples of wetting agents that can be used are fatty alcohols, esters and ethers. Preferably, the wetting agent is a hydrophilic, non-ionic surfactant, most preferably polyoxyethylene (20) sorbitan monooleate (supplied as the branded product Polysorbate 80).

Suitable viscosity enhancing agents include carboxymethylcellulose, veegum, tragacanth, bentonite, hydroxypropylmethylcellulose, hydroxypropylcellulose, hydroxyethylcellulose, poloxamers (eg. poloxamer 407), polyethylene glycols, alginates xanthym gums, carageenans and carbopols.

Suitable isotonicity adjusting agents act such as to achieve isotonicity with body fluids (e.g. fluids of the nasal cavity), resulting in reduced levels of irritancy associated with many nasal formulations. Examples of suitable isotonicity adjusting agents are sodium chloride, dextrose and calcium chloride.

Suitable thixotropic agents include that sold under the trade name Avicel RC951 NF, which comprises a mixture of carboxymethylcellulose sodium salt (8.3% to 13.8%) and microcrystalline cellulose. Thixotropic agents tend to make the formulation more viscous when static, but to become less viscous when kinetic energy is applied (e.g. on shaking the container).

In another aspect, the fluid medicament formulation is formulated as a solution medicament formulation. The formulation may be an aqueous, or in particular embodiments, a non-aqueous formulation. Suitable solution formulations may comprise a solubilising agent such as a surfactant.

Suitable surfactants include $\alpha$-[4-(1,1,3,3-tetramethylbutyl)phenyl]-$\omega$- hydroxypoly(oxy-1,2-ethanediyl) polymers including those of the Triton series e.g. Triton X-100, Triton X-114 and Triton X-305 in which the X number is broadly indicative of the average number of ethoxy repeating units in the polymer (typically around 7-70, particularly around 7-30 especially around 7-10) and 4-(1,1,3,3-tetramethylbutyl)phenol polymers with formaldehyde and oxirane such as those having a relative molecular weight of 3500-5000 especially 4000-4700, particularly Tyloxapol. The surfactant is typically employed in a concentration of around 0.5-10%, preferably around 2-5% w/w based on weight of formulation.

Suitable solution formulations may also comprise hydroxyl containing organic co-solvating agents include glycols such as polyethylene glycols (eg PEG 200) and propylene glycol; sugars such as dextrose; and ethanol. Dextrose and polyethylene glycol (eg PEG 200) are preferred, particularly dextrose. Propylene glycol is preferably used in an amount of no more than 20%, especially no more than 10% and is most preferably avoided altogether. Ethanol is preferably avoided. The hydroxyl containing organic co-solvating agents are typically employed at a concentration of 0.1-20% e.g. 0.5-10%, e.g. around 1-5% w/w based on weight of formulation.

Suitable solution formulations may also comprise solublising agents such as polysorbate, glycerine, benzyl alcohol, polyoxyethylene castor oils derivatives, polyethylene glycol and polyoxyethylene alkyl ethers (e.g. Cremophors, Brij). Other solubilising agents are those sold under the trade name Miglyol by Condea Chemie GmbH wich comprise ester oils of saturated coconut and plam oil-derived caprylic and capric fatty acids and glycerin or propylene glycol.

One non-aqueous solution formulation is based upon Miglyol (trade name) either used neat to solubilise the medicament substance, or as a mixture with propylene glycol and/or polyethylene glycol.

Suitable suspension or solution formulations may be stabilised (e.g. using hydrochloric acid or sodium hydroxide) by appropriate selection of pH. Typically, the pH will be adjusted to between 4.5 and 7.5, preferably between 5.0 and 7.0, especially around 6 to 6.5.

The fluid medicament formulation herein suitably has a viscosity of from 10 to 2000 mPa·s (10 to 2000 centipoise), particularly from 20 to 1000 mPa·s (20 to 1000 centipoise), such as from 50 to 1000 mPa·s (50 to 1000 centipoise) at 25° C.

The viscosity of the inert suspending formulation herein is measured by any suitable method.

The dispensing device herein is suitable for dispensing fluid medicament formulations for the treatment of inflammatory and/or allergic conditions of the nasal passages such as rhinitis e.g. seasonal and perennial rhinitis as well as other local inflammatory conditions such as asthma, COPD and dermatitis.

A suitable dosing regime would be for the patient to inhale slowly through the nose subsequent to the nasal cavity being cleared. During inhalation the formulation would be applied to one nostril while the other is manually compressed. This procedure would then be repeated for the other nostril. Typically, one or two inhalations per nostril would be administered by the above procedure up to three times each day, ideally once daily. Each dose, for example, may deliver 5 µg, 50 µg, 100 µg, 200 µg or 250 µg of active medicament. The precise dosage is either known or readily ascertainable by those skilled in the art.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A nasal dispensing nozzle for use with a fluid medicament discharge pump device having a discharge outlet for discharge of pumped fluid medicament, the nasal dispensing nozzle comprising a body defining a fluid flow channel;

an inlet port defining an inlet to said channel, said inlet port shaped for receipt of said discharge outlet to enable delivery of said pumped fluid medicament to the channel;

an outlet port defining an outlet from said channel, said outlet port shaped for insertion into the nasal cavity of a user to enable delivery of the pumped fluid medicament thereto, and an insert comprising a body and screw thread on the body which provides the insert with a screw thread outer surface of constant diameter, the insert being positioned in the channel with the screw thread engaging a wall of the channel to provide a screw thread path to the channel between the inlet and said outlet to impart angular momentum to the pumped fluid medicament, wherein one of the channel wall and the insert body has a tapered profile and the other is of constant diameter such that the screw thread path decreases in cross-sectional area from the entrance to the exit thereto.

2. A nasal dispensing nozzle according to claim 1, wherein the body further defines a hollow chamber locating between the screw thread path and the outlet port.

3. A nasal dispensing nozzle according to claim 1, wherein the screw thread path defines at least three complete screw turns.

4. A nasal dispensing nozzle according to claim 1, wherein the screw thread path extends in symmetric fashion about a screw thread axis.

5. A nasal dispensing nozzle according to claim 4, wherein the screw thread axis corresponds to the pumping axis of the fluid medicament discharge pump device.

6. A nasal dispensing nozzle according to claim 4, wherein the fluid flow channel is symmetric about the screw thread axis.

7. A nasal dispensing nozzle according to claim 4, wherein the body of the nozzle is symmetric about the screw thread axis.

8. A nasal dispensing nozzle according to claim 1, wherein the screw thread path comprises plural screw threaded pathways.

9. A nasal dispensing nozzle according to claim 8, wherein each screw threaded pathway is arranged about a common screw thread axis.

10. A nasal dispensing nozzle according to claim 8, wherein the screw thread path comprises from two to eight screw threaded pathways.

11. A nasal dispensing nozzle according to claim 1, wherein the depth of the screw thread path progressively reduces from the entrance to the exit.

12. A nasal dispensing nozzle according to claim 1, wherein the width of the screw thread path progressively reduces from the entrance to the exit.

13. A nasal dispensing nozzle according to claim 1, wherein the pitch of the screw thread path progressively reduces from the entrance to the exit.

14. A housing assembly for reversible receipt of a fluid medicament discharge pump device for spraying a fluid medicament into a nasal cavity, the housing assembly comprising a body defining a cavity; and engageable with said body, a dispensing nozzle according to claim 1.

15. A fluid medicament dispensing device comprising a housing assembly according to claim 14 and received thereby, a fluid medicament discharge pump device.

16. A kit of parts comprising a housing assembly according to claim 14 and a fluid medicament discharge pump device receivable thereby.

17. A fluid medicament dispensing device according to claim 15, wherein the fluid medicament discharge pump device comprises a hollow casing defining a reservoir for containing a volume of fluid medicament and a pump having a suction inlet extending within the hollow casing, the pump having a discharge outlet extending from a first end of the hollow casing for co-operation with the dispensing nozzle to enable pumped delivery of fluid from the reservoir to the dispensing nozzle.

18. A fluid medicament dispensing device according to claim 15, wherein said reservoir contains a volume of fluid medicament formulation.

19. A nasal dispensing nozzle according to claim 1, wherein the channel is of constant diameter, the channel wall is smooth and the insert body is tapered.

20. A nasal dispensing nozzle according to claim 1, wherein the channel wall is tapered and has a screw thread surface defined therein which receives the screw thread of the insert and the body of the insert has a constant diameter.

* * * * *